US008801682B2

(12) United States Patent
Kensy

(10) Patent No.: US 8,801,682 B2
(45) Date of Patent: Aug. 12, 2014

(54) APPARATUS FOR SEPARATING TISSUE CELLS FROM A FLUID

(75) Inventor: Arnd Kensy, Michendorf (DE)

(73) Assignee: Human Med AG, Schwerin (DE)

( * ) Notice: Subject to any disclaimer, the term of this patent is extended or adjusted under 35 U.S.C. 154(b) by 493 days.

(21) Appl. No.: 12/817,428

(22) Filed: Jun. 17, 2010

(65) Prior Publication Data

US 2011/0183406 A1 Jul. 28, 2011

Related U.S. Application Data

(60) Provisional application No. 61/304,503, filed on Feb. 15, 2010.

(30) Foreign Application Priority Data

Jan. 27, 2010 (DE) .......................... 10 2010 001 292

(51) Int. Cl.
*A61M 1/00* (2006.01)
*A61M 1/02* (2006.01)
*C12M 1/00* (2006.01)

(52) U.S. Cl.
CPC .............. *A61M 1/0001* (2013.01); *A61M 1/00* (2013.01); *A61M 2202/08* (2013.01); *A61M 1/029* (2013.01); *A61M 1/0056* (2013.01); *C12M 47/04* (2013.01); *C12M 47/02* (2013.01); *A61M 2202/09* (2013.01)
USPC ............. 604/317; 604/319; 604/414; 604/19; 604/542; 210/455; 210/435; 210/232; 210/416.1

(58) Field of Classification Search
CPC . A61M 1/0001; A61M 1/00; A61M 2202/08; A61M 1/029; A61M 2202/09; C12M 47/04; C12M 47/02
USPC .............. 604/319, 414, 542; 210/416.1, 455, 210/435, 94, 232
See application file for complete search history.

(56) References Cited

U.S. PATENT DOCUMENTS

| 2,936,757 A | 4/1957 | Trace |
| 3,685,517 A | 8/1972 | Reynolds et al. |
| 5,624,418 A * | 4/1997 | Shepard ........................ 604/319 |
| 8,100,874 B1 * | 1/2012 | Jordan et al. ................... 604/319 |
| 2009/0116714 A1 * | 5/2009 | Richmond et al. ............ 382/129 |

FOREIGN PATENT DOCUMENTS

| DE | 689 23 464 T2 | 3/1996 |
| EP | 0 384 585 A1 | 8/1990 |
| EP | 1 837 045 A1 | 9/2007 |
| EP | 2 119 461 A2 | 11/2009 |
| WO | 2009/149691 A2 | 12/2009 |

\* cited by examiner

*Primary Examiner* — Nathan Bowers
(74) *Attorney, Agent, or Firm* — Norris McLaughlin & Marcus PA

(57) ABSTRACT

The invention relates to an apparatus for separating tissue cells from a fluid, with a collection container forming a collection space, which is connected, on one hand, with a negative pressure source and which is connected, on the other hand, with a supply line for the fluid-tissue cell mixture.

Figure 1:
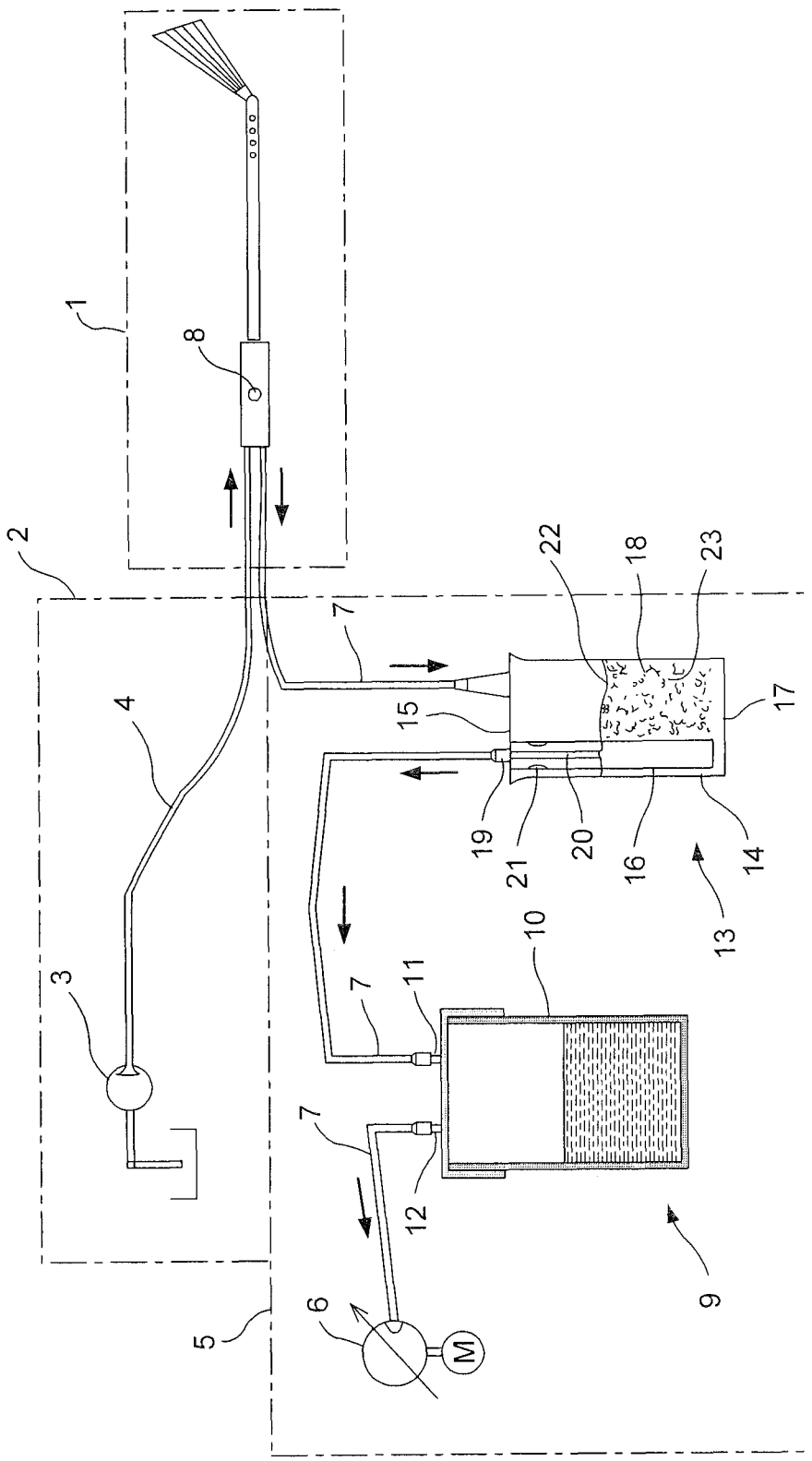

It is provided that inside the collection space (18) a communicating tube (16) is arranged, which terminates at a distance from the bottom (17) of the collection container (14), wherein a connection is provided between the communicating tube (16) and the collection space (18) above a fluid-tissue cell mixture level (22) established in the collection container (14), and a suction element (20) which is connected with the negative pressure source (6) is arranged inside the communicating tube (16).

5 Claims, 4 Drawing Sheets

APPARATUS FOR SEPARATING TISSUE CELLS FROM A FLUID

The invention relates to an apparatus for separating tissue cells from a fluid, with a collection container forming a collection space, wherein the collection container is connected, on one hand, with a negative pressure source and, on the other hand, with a supply line for a fluid-tissue cell mixture.

Apparatuses of this type are known in the art. For example, WO 2009/149691 A2 discloses a method and an apparatus for separating tissue cells from a fluid, wherein a tissue cell collector under vacuum includes a filter unit which divides the collection container into a lower collection space for the fluid, a center collection space for the tissue cells, and an upper vacuum space. The lower collection space for the fluid and the upper vacuum space are interconnected with one another, bypassing the collection space for the tissue cells.

It is an object of the invention to provide an apparatus of the generic type which has a simple structure and enables gentle separation of the tissue cells from a fluid-tissue cell mixture.

This object is solved according to the invention with an apparatus having the features recited in claim 1. A particularly simple and gentle separation of the withdrawn tissue cells from the fluid can be achieved by arranging inside the collection space a communicating tube, which terminates at a distance from the bottom of the collection container, wherein a connection is established between the communicating tube and the collection space above a resulting fluid-tissue cell mixture level, and wherein a suction element connected with a negative pressure source is arranged inside the communicating tube. Gentle separation is particularly important for reprocessing tissue cells previously removed from a human body so that they are later suitable, for example, for reintroduction into the human body. The fluid can be suctioned off with the applied negative pressure using the communicating tube inserted into the collection space, in particular with the suction element arranged inside the communicating tube, whereas the tissue cells settle in the collection space. The tissue cells have a lower density than the fluid, so that they are propelled to the surface by buoyancy forces. Because the communicating tube is inserted in the collection container as close to the bottom as possible, the fluid level established in the communicating tube is at the same level as the fluid level in the collection space. The cells then remain in the collection space, whereas the fluid rises in the communicating tube, from where it is suctioned off by the inserted suction element. With the subsequently supplied fluid-tissue cell mixture, the same fluid level is established in the communicating tube as in the collection space. The connection between the communicating tube and the collection space above a fluid-tissue cell mixture level ensures that a pressure equilibrium is established in the communicating tube and the collection space, utilizing here the effect of the communicating tube where the fluid is suctioned off and the tissue cells remain in the collection space. This ensures supply of the fluid-tissue cell mixture into the collection space and enables, on the other hand, gentle separation of the fluid from the tissue cells.

In a preferred embodiment of the invention, a very narrow collection container having the greatest possible height and the smallest possible diameter should be used for collecting a fluid-tissue cell mixture. This design takes advantage of the buoyancy of the tissue cells in the fluid mixture.

The communicating tube arranged in the collection space has an opening into the collection space located above the suction opening of the enclosed suction element. This opening is responsible for rapid pressure equalization between the communicating tube with the enclosed suction element and the collection space. The greater the opening, the smaller the effective suction on the fluid level in the communicating tube. This positively affects the level equalization and affords the fluid-tissue cell mixture in the collection space more time for the cell separation through buoyancy.

Moreover, the communicating tube arranged in the collection space has the smallest possible spacing relative to the container bottom. The resulting gap provides level equalization between the fluid-tissue cell mixture in the collection space and the rising fluid in the communicating tube. The configuration of the gap is also responsible for correctly separating the tissue cells from the residual fluid mixture. A small gap has a throttle function which positively affects the level equalization, meaning that the fluid-tissue cell mixture in the collection space is afforded more time for cell separation through buoyancy.

When the fluid-tissue cell mixture is initially suctioning off, i.e., when there is not yet any mixture in the container, the desired pressure conditions inside the collection container are quickly established. Due to the structure of the collection container, a mostly tissue-free fluid region is immediately formed, causing via the gap between the container bottom and the communicating tube a level equalization between the fluid-tissue cell mixture in the collection space and the interior space of the communicating tube. When suction continues and the fluid-tissue cell mixture level in the collection space and in the communicating tube rises, the suction element surrounded by the communicating tube dips becomes immersed in the fluid to be suctioned off. To give the fluid-tissue cell mixture additional time for cell separation through buoyancy, the fluid is only now suctioned off by opening the suction element, with the fluid transported via the suction line into the fluid container.

At the end of the suctioning process, when a desired quantity of tissue cells has been collected in the collection space, the tissue-free fluid region above the container bottom and in the communicating tube can be decreased depending on the adjusted insertion depth of the suction element, until ideally only tissue cells are present in the collection container.

In another preferred embodiment of the invention, the communicating tube has at the end facing the bottom openings which are open at the edges. In this way, the communicating tube can advantageously be supported with its lower end of the bottom of the collection container, while the openings open at the edges provide passageways for fluid flow from the collection space into the communicating tube. In addition to supporting the tube in the cover, the support on the bottom produces a particularly stable apparatus adapted for harsh operating conditions.

Moreover, in a preferred embodiment of the invention, a mouth of the suction element is located below the passageway located above the fluid-tissue cell mixture level between the communicating tube and the collection space. In this way, a greatest possible volume can advantageously be provided inside the collection container for collecting the tissue cells. This connection between the collection space and the communicating tube is therefore located above the suction mouth of the suction element.

In still another preferred embodiment of the invention, the suction element has a variable length and/or its length can be variably adjusted. In this way, the apparatus can advantageously be adapted to different quantities of tissue cell to be collected. The shorter the suction element, the later it comes into contact with the fluid level in the communicating tube. In other words, a larger quantity of the fluid-tissue cell mixture initially enters the collection space, before the fluid is suctioned off. The tissue cells then have also more time to accumulate on the surface of the fluid due to the buoyancy effect, with the fluid then subsequently being suctioned off from below via the communicating tube. Moreover, larger quantities of tissue cells can thereby be collected than with a longer suction element.

In addition, in another preferred embodiment of the invention, the collection container may include a closable removal opening for the collected tissue cells. Advantageously, the tissue cells collected in the collection space can then be advantageously removed gently and without problems, for example by suction. Consequently, the entire apparatus need not be detached from the negative pressure source and the device for supplying the fluid-tissue cell mixture. The suction process of the fluid-tissue cell mixture can be briefly interrupted for removing the accumulated tissue cells and can subsequently be continued without requiring reinstallation. In this way, the apparatus of the invention can be particularly effectively utilized.

Finally, according to another preferred embodiment of the invention, the collection container is closable with a lid, which has an opening for connecting the negative pressure source by way of the adjustable suction element, an opening for connecting the supply line of the fluid-tissue cell mixture and the closable removal opening. In this way, all functional connection elements can be integrated in the lid, with the overall collection container then having a simple structure which can also be manufactured cost-effectively in large quantities.

Moreover, according to a preferred embodiment of the invention, the lid includes on its side that faces the collection space attachment means for a catch basket which is arranged below the opening where the supply line for the fluid-tissue cell mixture is connected. In this way, the catch basket advantageously provides a gentle transfer of the fluid-tissue cell mixture into the collection space. This mixture then the longer impinges with a large velocity on the already collected tissue cells, but is first calmed down by the catch basket forming a flow resistance, and thereafter controllably flows into the collection space. Undesirable tissue fractions, for example connecting tissue, are filtered out by the catch basket and hence do not enter the collection space.

The materials of the apparatus of the invention, in particular the collection container, the lid, the communicating tube, the suction element and the catch basket as well as the required fittings and connecting pieces are made of a material suitable for clinical applications, for example plastic and/or metal.

Additional preferred embodiments of the invention can be inferred from the additional features recited in the dependent claims.

Figure 2:
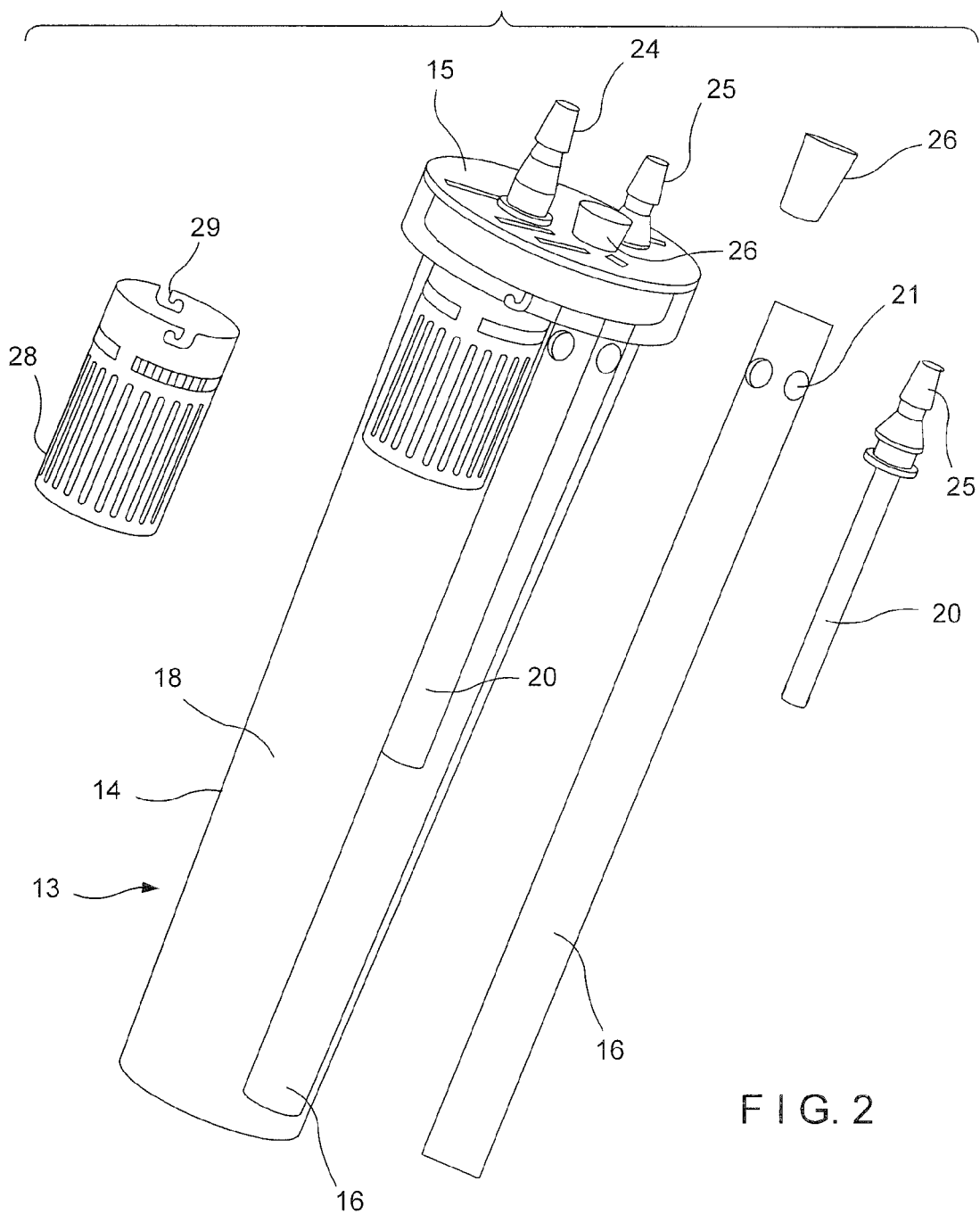
Figure 3:
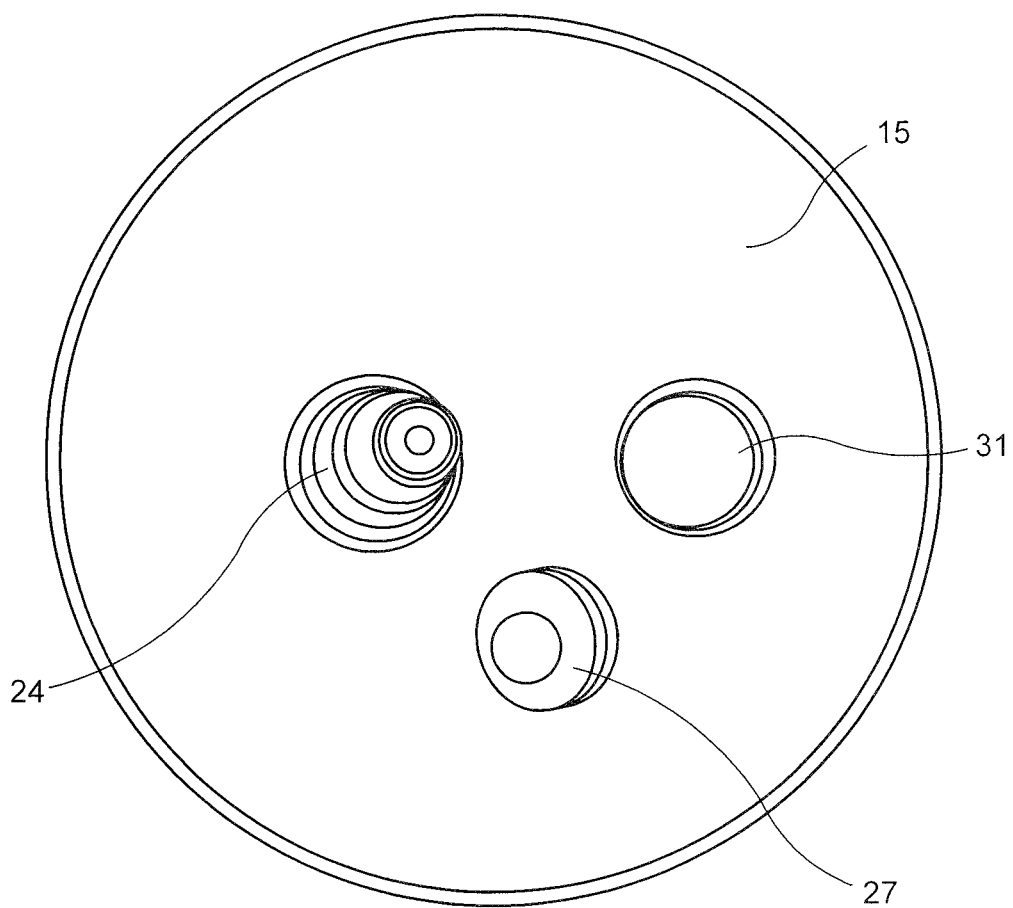

An exemplary embodiment of the invention will now be described in more detail with reference to the appended drawings. These show in:

FIG. 1 a schematic diagram of a device for fluid jet separation with an integrated apparatus according to the invention for separating tissue cells from a fluid;

FIG. 2 a schematic perspective view of the apparatus of the invention for separating tissue cells, in an assembled state and in an exploded view;

FIG. 3 a top view onto a lid of the apparatus according to FIG. 2; and

Figure 4:
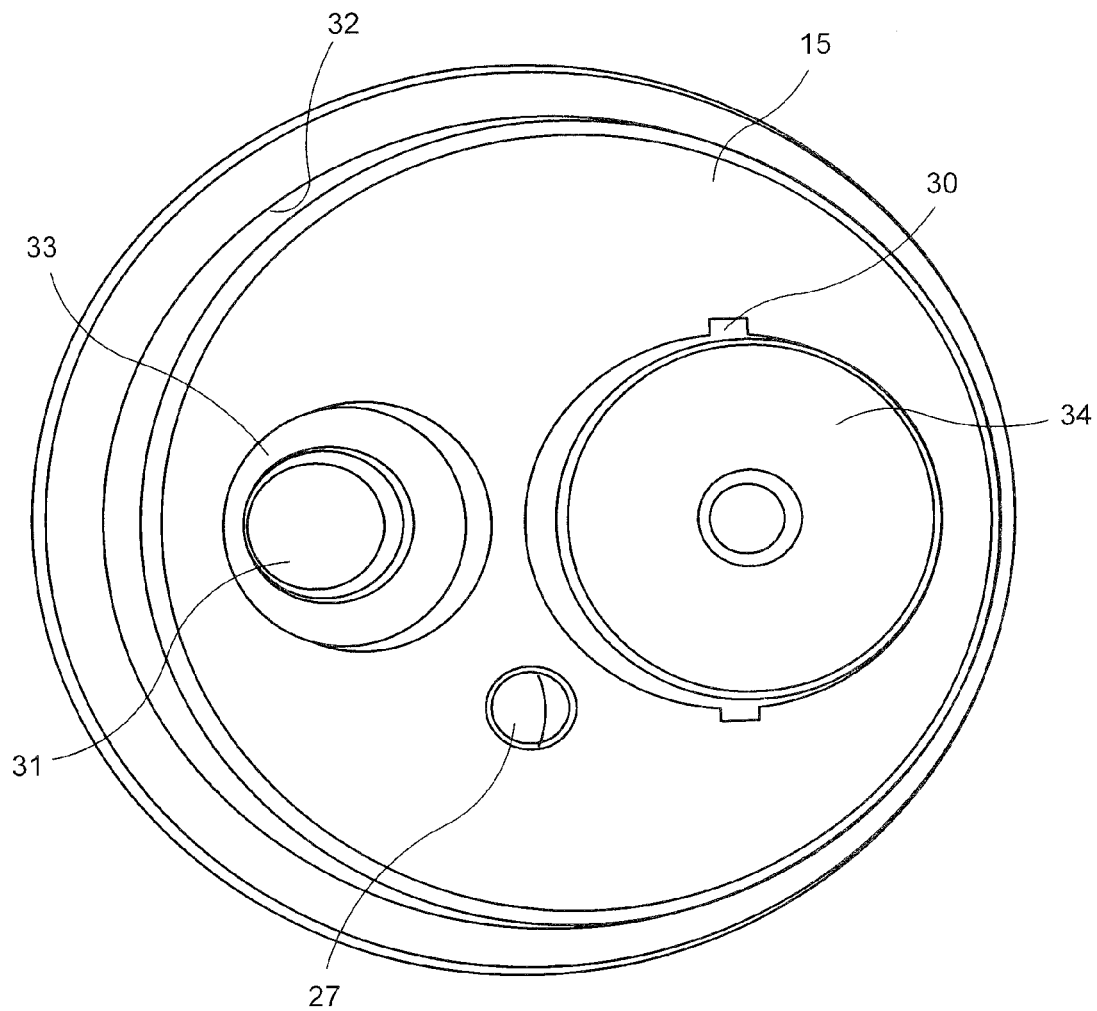

FIG. 4 a bottom view onto the lid according to the apparatus of FIG. 2.

FIG. 1 shows a device for fluid jet separation with an applicator 1, which can be operated manually by an operator, for water-jet-supported separation and suctioning of tissue cells from a biological structure, with a pressurized jet device 2, with a pressure generator 3 and a pressure line 4 for supplying the applicator 1 with a defined fluid jet, as well as a suction device 5 for removing from the body 1 the separated tissue parts (tissue cells) and the spent working fluid and the fluid produced naturally in the body. The suction device 5 includes a vacuum generator 6 and a suction line 7, wherein the suction line 7 provides a continuous connection between the vacuum generator 6 and the applicator 1. The suction line 7 has in the region of the applicator 1 a closable bypass 8 connecting the suction line 7 to atmosphere. A residual fluid collector 9 for the suctioned fluid, having a closable receiving container 10 as well as an inlet fitting 11 and an outlet fitting 12 for the suction line 7, is located in the suction line 7. The residual fluid collector 9 for the filtered fluid is arranged upstream of the vacuum generator 6 in the suction direction. A tissue cell collector 13 is interconnected in the suction line 7 between the residual fluid collector 9 and the applicator 1.

The tissue cell collector 13 is made of a cylindrical collection container 14 which is closed pressure-tight with a lid 15. The collection container 14 has preferably a cylindrical shape. Preferably, the collection container 14 is transparent to allow observation of the fluid level and evaluation of the condition of the collected tissue cells. For observing the fill level, the collection container 14 has a fill level gauge.

A communicating tube 16 is arranged in the collection container 14. The communicating tube 16 terminates at a distance above the bottom 17 of the collection container 14. In this way, a (lower) connection is formed between the communicating tube 16 and a collection space 18 inside the collection container 14. The communicating tube 16 is attached to the lid 15 and surrounds a fitting 19 for the suction line 7 in the direction towards the vacuum generator 6 (negative pressure source). The communicating tube 16 surrounds an opening (not shown in FIG. 1) for connection of the suction line 7. This opening is directly connected with a suction element 20 which extends into the communicating tube 16. The communicating tube 16 has at least one opening 21 providing an (upper) connection between the interior space of the communicating tube 16 and the collection space 18. This at least one opening 21 is located above an indicated level 22 of a fluid-tissue cell mixture 23 inside the collection container 14. The length of the suction element 20 determines the height of the level 22.

The device for fluid jet separation illustrated in FIG. 1 exhibits the following function:

When applying the fluid jet separation method, a defined fluid separation jet exits the applicator 1, with the effect of the fluid separation jet determined by the fluid pressure produced in the pressurized jet device and the design of the applicator 1. This effect is intended to gently separate tissue cells from a biological structure. The separated tissue cells together with the injected working fluid and the other fluids produced naturally in the body are suctioned off by a vacuum generated in the suction device 5. This method is frequently used with liposuction. The suctioned tissue cells are always separated from the fluid-tissue cell mixture if the tissue cells are to be reused. This is performed with the tissue cell collector 13.

In a standby position, the operator holds the closable bypass 8 open, thereby preventing any suction, with only atmospheric air being sucked in and transported through the tissue cell collector 13. The air hereby passes through the tissue cell collector 13 towards the vacuum generator 6 via the upper region of the collection space 18, the communicating tube 16 with the opening 21, and the suction element 20.

In an operating position, the closable bypass 8 is closed by the operator, so that the suction force from the vacuum generator 6 is transferred to the operating field. In this way, the separated tissue parts (tissue cells) and the various fluids are received and transported to the tissue cell collector 13. In the tissue cell collector 13, this mixture composed of tissue cells and fluid reaches the collection space 18 via the inlet fitting. The level of the fluid-tissue cell mixture 23 rises inside the collection space 18, whereby the tissue cells experience a buoyancy force due to their lower density and rise inside the fluid-tissue cell mixture 23 to the surface, i.e., in the direction of the level 22. The level in the collection space 18 is the same as in the communicating tube 16. Essentially only the fluid of the fluid-tissue cell mixture 23 rises in the communicating tube through the connection between the lower end of the communicating tube proximate to the bottom 17 and the collection space 18. The tissue cells remain in the collection space 18, while the fluid rises in the communicating tube 16. After the level 22 has risen to a point where it reaches the mouth of the suction element 20, the fluid is suctioned off inside the communicating tube in the direction towards the receiving container 10. This process continues until the desired or the maximum quantity of tissue cells is collected in the collection space 18. It is evident that the length of the suction element 20 affects the height of the level 22. The shorter the suction element 20, the higher the level 22 may be inside the collection container 14 and the larger the collectable quantity of tissue cells inside the collection space 18.

Pressure equalization between the collection space 18 and the communicating tube is achieved via the at least one opening 21 between the communicating tube 16 and the collection space 18, so that the fluid in the communicating tube—according to the principle of communicating tubes—rises to the same level as the fluid-tissue cell mixture 23 in the collection space 18.

The unobstructed cross-section between the communicating tube 16 in the region of the bottom 17 and the collection space 18 is sized so small that only the fluid, but essentially no tissue cells can reach the communicating tube 16 through this unobstructed cross-section. According to an unillustrated exemplary embodiment, the communicating tube 16 can have openings disposed at its lower end which are open at the edges, so that the tube 16 can be supported on the bottom 17, while still leaving an unobstructed cross-section between the communicating tube 16 and the collection space 18 for transfer of the fluid.

FIG. 2 shows a schematic perspective view of the collection container 14, in an assembled state and also in a diagram showing individual parts. Parts identical to those in FIG. 1 have the same reference symbols and will not be described again.

It is evident that the collection container 14 is closed pressure-tight by the lid 15. The lid 15 has a connecting element 25 for connection with the receiving container 10 via the suction line 7. Also shown is a connecting element 24 for connecting the suction line 7 in the direction towards the applicator 1. The connecting element 25 is connected with the suction element 20. Also shown is a stopper 26 for closing an opening 27 (FIG. 3) in the lid 15. Also indicated is the communicating tube 16 inside which the suction element 20 is arranged. The communicating tube 16 has the opening 21 for providing an (upper) connection with the collection space 18.

FIG. 2 also shows a catch basket 28 which can be attached on the bottom side of the lid 15. The catch basket 28 has snap-in connections 27, similar to a bayonet catch, engaging with corresponding pegs 30 (FIG. 4) disposed on the bottom side of the lid. The catch basket 28 is substantially cylindrical and has circumferential openings. The catch basket 28 is arranged directly below the fitting 24. In this way, the fluid-tissue cell mixture 23 suctioned off through the applicator 1 first reaches the catch basket 28 and therefrom the actual collection space 18. The catch basket 28 is used for calming the fluid-tissue cell mixture 23 which reaches the collection container 14 via the suction line 7. As a result, the tissue cells already collected in the collection space 18 are not directly stressed by the fluid-tissue cell mixture 23 introduced with the flow.

FIGS. 3 and 4 show the lid 15 in a top view and a bottom view. The top view of FIG. 4 clearly shows the opening 27 in which the stopper 26 for pressure-tight closure can be inserted. To this end, matching conical contact faces are provided. When the stopper 26 is removed, the opening 27 provides access to the collection space 18. The tissue cells accumulated in the collection container 14 can be removed with a suitable suction wand and the like, or transported onward for further processing.

Also visible is an opening 31, into which the connecting element 25 with the attached suction element 20 is inserted from the top side of the lid 15 with a pressure-tight fit. The connecting element 24 attached to the lid 15, which provides the connection via the suction line 7 to the applicator 1, is also visible.

FIG. 4 shows the bottom view from below the lid 15, indicating that the lid 15 has a circumferential ring-shaped step 32 which enables pressure-tight insertion into the collection container 14. As can also be seen, a ring-shaped indentation 33 is arranged about the opening 31. This indentation 33 is contacted by the communicating tube 16, which is then held in place by the lid 15. The connecting element 25 also passes through the opening 31, where it is secured pressure-tight. Visible on the bottom side of the lid 15 is a downwardly protruding region 34 which includes diametrically opposed bolts 30 for receiving the catch basket 28.

LIST OF REFERENCES SYMBOLS

1 Applicator
2 Pressurized jet device
3 Pressure generator
4 Pressure line
5 Suction device
6 Vacuum generator
7 Suction line
8 Bypass
9 Residual fluid collector
10 Receiving container
11 Inlet fitting
12 Outlet fitting
13 Tissue cell collector
14 Collection container
15 Lid
16 Communicating tube
17 Bottom
18 Collection space
19 Fitting
20 Suction element
21 Opening
22 Level
23 Fluid-tissue cell mixture
24 Connecting element
25 Connecting element
26 Stopper
27 Opening
28 Catch basket
29 Snap-in connection
30 Peg/bolt
31 Opening 32 Ring-shaped step
33 Ring-shaped indentation
34 Protruding region

The invention claimed is:

1. Apparatus for separating tissue cells from a fluid, with a collection container forming a collection space, the collection container (14) has a closable removal opening (27) for the collected tissue cells, the collection container (14) is closable with a lid (15) which has an opening (31) for connecting a negative pressure source, a connecting element (24) for connecting a supply line for the fluid-tissue cell mixture (23) and the closable removal opening (27), wherein inside the collection space (18) a communicating tube (16) is arranged, which terminates at a distance from the bottom (17) of the collection container (14), wherein the communicating tube (16) has at least one opening (21) providing a connection between the interior space of the communicating tube (16) and the collection space (18) above a fluid-tissue cell mixture level (22) established in the collection container (14), and wherein a suction element (20) which is connected with the negative pressure source (6) is arranged inside the communicating tube (16).

2. Apparatus according to claim 1, wherein the distance between the communicating tube (16) and the bottom (17) of the collection container (14) is selected, such that an unobstructed cross-section between the communicating tube (16) and collection space (18) at the bottom (17) is smaller than an unobstructed cross-section of the connection (21) between the communicating tube (16) and the collection space (18) above the fluid-tissue cell mixture level (22).

3. Apparatus according to claim 1, wherein the communicating tube (16) has at its end facing the bottom (17) openings which are open towards the edge.

4. Apparatus according to claim 1, wherein the suction element (20) has a variable length and/or can be adjusted to have a variable length.

5. Apparatus according to claim 1, wherein the lid (15) comprises on its side facing the collection space (18) attachment means (30) for a catch basket (28).

* * * * *